United States Patent [19]

Treuner

[11] 4,260,751

[45] Apr. 7, 1981

[54] PYRAZOLO [1,2-a][1,2,4] BENZOTRIAZINES

[75] Inventor: Uwe D. Treuner, Regensburg, Fed. Rep. of Germany

[73] Assignee: E. R. Squibb & Sons, Inc., Princeton, N.J.

[21] Appl. No.: 144,482

[22] Filed: Apr. 28, 1980

[51] Int. Cl.³ .................................... C07D 487/04
[52] U.S. Cl. .................................... 544/183
[58] Field of Search ........................... 544/183

[56] References Cited

U.S. PATENT DOCUMENTS

| | | | |
|---|---|---|---|
| 3,349,088 | 10/1967 | Molnar et al. | 260/248 |
| 3,994,893 | 11/1976 | Treuner | 260/250 Q |
| 4,022,782 | 5/1977 | Treuner | 260/268 M |
| 4,033,958 | 7/1977 | Treuner | 260/247.2 B |
| 4,052,393 | 10/1977 | Treuner | 260/250 Q |
| 4,072,680 | 2/1978 | Denzel et al. | 260/256.4 F |
| 4,077,956 | 3/1978 | Treuner | 260/250 BC |
| 4,128,716 | 12/1978 | Treuner | 544/346 |

OTHER PUBLICATIONS

Mixich, *Helvetica Chimica Acta*, vol. 51, Fasciculus 3, pp. 532-538 (1968).
Merck Index, 9th Ed. (1976), p. 99.

*Primary Examiner*—John M. Ford
*Attorney, Agent, or Firm*—Lawrence S. Levinson; Dale Lovercheck

[57] ABSTRACT

Pyrazolo[1,2-a][1,2,4] benzotriazines having the formula

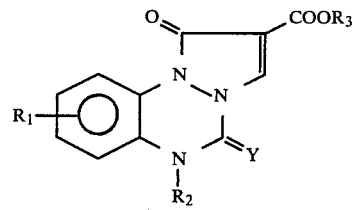

wherein
$R_1$ is hydrogen, lower alkyl, nitro, amino, lower alkylamino, di(lower alkyl)amino, $-SR_4$, $-OR_4$ or halogen;
$R_2$ is hydrogen, lower alkyl or aralkyl;
$R_3$ is hydrogen, lower alkyl or a salt forming ion;
$R_4$ is hydrogen or lower alkyl; and Y is oxygen or sulfur.

The compounds are useful as intermediates and as antiinflammatory agents.

10 Claims, No Drawings

PYRAZOLO [1,2-A][1,2,4] BENZOTRIAZINES

BACKGROUND OF THE INVENTION

Molnar et al. in U.S. Pat. No. 3,349,088 disclose compounds of the formula wherein
- $X^1$ and $X^2$ are hydrogen, halogen, lower alkyl, lower alkoxy or lower alkylamino;
- Y is amino, lower alkylamino, lower alkoxy, phenyl, piperidino, morpholino lower alkyl and phenyl lower alkyl;
- $Z^1$ and $Z^2$ when linked together, represent the diacyl di-radical of an acid selected from the group consisting of lower aliphatic dibasic carboxylic acids and lower aliphatic dibasic carboxylic acid whose alkylene group is substituted with cycloalkyl.

Merck Index 9th ed. (1976) page 99 discloses Apazone having the formula as being anti-inflammatory.

Treuner in U.S. Pat. No. 4,128,716 discloses anti-inflammatory agents of the formula wherein
- $R_1$ is hydrogen lower alkyl or a salt forming ion;
- $R_2$ is hydrogen, lower alkyl, halogen or lower alkoxy and X is halogen.

Treuner in U.S. Pat. No. 4,033,958 discloses anti-inflammatory compounds of the formula wherein
- $R_1$ is hydrogen, lower alkyl or a salt forming ion;
- $R_2$ and $R_3$ each is hydrogen, lower alkyl, cyclolower alkyl, phenyl, substituted phenyl, phenyl-lower alkylene, di-lower alkylamino-lower alkylene or $R_2$ and $R_3$ together with the nitrogen form an unsubstituted or substituted 5- or 6-membered nitrogen heterocyclic in which an additional nitrogen or oxygen may be present.
- $R_4$ is hydrogen, lower alkyl or halogen.

Treuner in U.S. Pat. No. 4,052,393 discloses anti-inflammatory compounds of the formula wherein $R_1$ is hydrogen, lower alkyl or a salt forming ion; $R_2$ is hydrogen, lower alkyl, phenyl-lower alkylene or amino-lower alkylene; $R_3$ is hydrogen, lower alkyl, halogen or lower alkoxy; and X is oxygen or sulfur.

Treuner in U.S. Pat. No. 4,022,782 discloses anti-inflammatory 4-amino derivatives of pyrazolo[1,5-a]quinoxaline-3-carboxylic acid, esters and their salts having the formula wherein $R_1$ is hydrogen, lower alkyl or a salt forming ion; $R_2$ and $R_3$ each is hydrogen, lower alkyl, cyclolower alkyl, phenyl, substituted phenyl, phenyl-lower alkylene, di-lower alkylamino-lower alkylene or $R_2$ and $R_3$ together with the nitrogen form an unsubstituted or substituted 5- or 6-membered nitrogen heterocyclic in which an additional nitrogen or oxygen may be present.
$R_4$ is hydrogen, lower alkyl or halogen.

Treuner in U.S. Pat. No. 3,994,893 discloses antiinflammatory compounds similar to those in U.S. Pat. No. 4,022,782 discussed above.

Treuner in U.S. Pat. No. 4,077,956 discloses anti-inflammatory 5-substituted derivatives of dipyrazolo[1,5-a:4',3'-e]pyrazine-6-carboxylic acid esters and their salts having the formula $R^1$ is hydrogen, lower alkyl or phenyl-lower alkylene; $R^2$ and $R^3$ each is hydrogen or lower alkyl; X is oxygen or sulfur; and $R^4$ is hydrogen, lower alkyl, phenyl-lower alkylene or amino-lower alkylene.

Denzel et al. in U.S. Pat. No. 4,072,680 disclose antiinflammatory derivatives of pyrazolo[1,5-a]pyrido[3,2-e]pyrimidine having the general formula

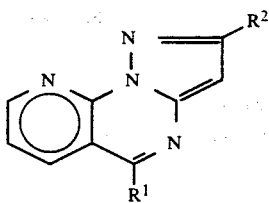

wherein
R[1] is lower alkoxy, lower alkylthio, amino, lower alkyl-amino or di(lower alkyl)amino.
R[2] is hydrogen or lower alkyl.

SUMMARY OF THE INVENTION

This invention relates to new pyrazolo[1,2-a][1,2,4]benzotriazines which have the formula

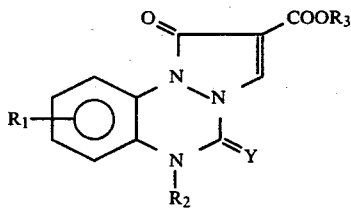

wherein
$R_1$ is hydrogen, lower alkyl, nitro, di(lower alkyl)amino, lower alkyl-amino, amino, $SR_4$, $OR_4$ or halogen;
$R_2$ is hydrogen, lower alkyl or aralkyl;
$R_3$ is hydrogen, lower alkyl or a salt forming ion; $R_4$ is hydrogen or lower alkyl; and Y is oxygen or sulfur.

The foregoing symbols have the same meaning throughout this specification.

DETAILED DESCRIPTION OF THE INVENTION

The lower alkyl groups are straight or branched chain hydrocarbons having up to seven carbon atoms in the chain, e.g. methyl, ethyl, propyl, isopropyl, butyl, isobutyl, t-butyl, amyl, hexyl heptyl etc. The $C_1$–$C_4$ lower alkyl groups are preferred and especially $C_1$–$C_2$ groups are preferred.

The halogens are the four common halogens but chlorine and bromine are preferred, especially the first.

The products of the examples are preferred embodiments.

Especially preferred compounds of formula I are those wherein
$R_1$ is hydrogen;
$R_2$ is hydrogen or lower alkyl, especially methyl or ethyl;
$R_3$ is lower alkyl, especially ethyl;
$R_4$ is hydrogen; and
Y is oxygen or sulfur.

The compounds of formula I are produced from a 2-nitrophenylhydrazine of the formula

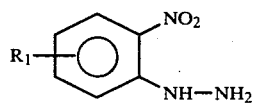

which is reacted with a compound of the formula

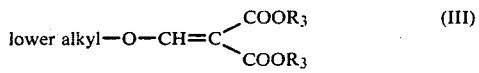

wherein $R_1$ and $R_2$ are as defined above. The resulting compound of the formula

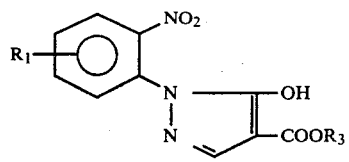

is hydrogenated in the presence of a catalyst like palladium on carbon producing a compound of the formula

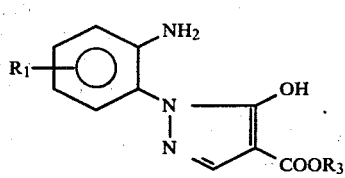

wherein $R_1$ and $R_3$ are as defined above. The compound of formula V is reacted with a compound of the formula

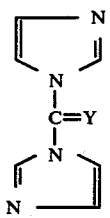

to form a compound of the formula

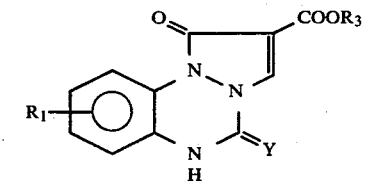

A compound of formula I wherein $R_2$ is lower alkyl or aralkyl is obtained by treating a compound of formula (VII) with a halolower alkyl or a haloaralkyl for example $CH_3I$.

Esters of formula I can be converted to the acid ($R_3$=H) by hydrolysis, e.g. with an equivalent of base like sodium or potassium hydroxide in an alcohol like ethanol.

Members of formula I wherein $R_3$ is hydrogen, form salts with metals, e.g. alkali metals like sodium, alkaline earth metals like calcium and magnesium etc., by treating an ester, i.e. $R_3$ is lower alkyl with an excess of base.

The hydrolysis and salt formation may be performed by following procedures known in the art see Treuner U.S. Pat. No. 4,128,716.

Additional experimental details are found in the Examples.

The compounds of formula I, have antiinflammatory properties and are useful for administration orally or parenterally as antiinflammatory agents, for example, to reduce local inflammatory conditions such as those of an edematous nature or resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the passive cutaneous anaphylaxis test in rats or delayed hypersensitivity skin reaction test.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can also be applied topically as antiinflammatory agents formulated in a conventional lotion, ointment, of cream containing about 0.1 to 3 percent by weight or a compound of formula I or its salt.

The following examples are illustrative of the invention and consitute preferred embodiments. They also serve as models for the preparation of other members of the group which can be produced by suitable substitution of starting materials. All temperatures are in °C.

EXAMPLE 1

5,6-Dihydro-1,5-dioxo-1H-pyrazolo[1,2-a][1,2,4]benzotriazine-2-carboxylic acid, ethyl ester (a)
5-Hydroxy-1-(2-nitrophenyl)-1H-pyrazole-4-carboxylic acid, ethyl ester.

102 g (2-nitrophenyl)hydrazine and 142 g (Ethoxymethylene)propanedioic acid, diethyl ester are dissolved in 300 ml ethanol and refluxed for 20 hours. After cooling the clear red solution is evaporated and the solvent distilled off. The remaining crystalline residue (168 g) is added to 400 g PPA (polyphosphoric acid) at a temperature of 80° C. The reaction is completed by heating the solution for 10 minutes to 120° C. The solution is then immediately poured on 2 kg ice and stirred for 30 minutes. After filtration the residue is recrystallized from n-propanol to yield 80 g of 5-hydroxy-1-(2-nitrophenyl)-1H-pyrazole-4-carboxylic acid, ethyl ester with a melting point of 157°–160° C.; yellow crystals.

(b)
1-(2-Aminophenyl)-5-hydroxy-1H-pyrazole-4-carboxylic acid, ethyl ester 126.3 g of 5-hydroxy-1-(2-nitrophenyl)-1H-pyrazole-4-carboxylic acid, ethyl ester is dissolved in 1.6 liter methanol and 1.2 g Pd/C (10%) are added and hydrogenation is performed until $H_2$-uptake is finished (12 hours). After filtration the solvent is distilled off and the crystalline residue is recrystallized from dimethylformamide/ethanol to yield 78 g of 1-(2-aminophenyl)-5-hydroxy-1H-pyrazole-4-carboxylic acid, ethyl ester as white powder having a melting point of 151°–154° C.

(c)
5,6-Dihydro-1,5-dioxo-1H-pyrazolo[1,2-a][1,2,4]benzotriazine-2-carboxylic acid, ethyl ester 24.7 g 1-(2-aminophenyl)-5-hydroxy-1H-pyrazole-4-carboxylic acid, ethyl ester and 16.2 g 1,1'-carbonyl-bis-[1H-imidazole] are dissolved in 300 ml tetrahydrofuran and stirred for 8 hours at room temperature and one hour at 90° C. The solid residue, after distilling off the solvent, is recrystallized from dimethylformamide to yield 21 g of 5,6-dihydro-1,5-dioxo-1H-pyrazolo[1,2-a][1,2,4]-benzotriazine-2-carboxylic acid, ethyl ester having a melting point of 269°–271° C.; white-yellow crystals.

EXAMPLE 2

5,6-Dihydro-1-oxo-5-thioxo-1H-pyrazolo[1,2-a][1,2,4]benzotriazine-2-carboxylic acid, ethyl ester 2.47 g 1-(2-aminophenyl)-5-hydroxy-1H-pyrazole-4-carboxylic acid, ethyl ester and 1.78 g 1,1'-thiocarbonyl-bis-[1H-imidazole] are dissolved in 50 ml tetrahydrofuran and heated for 8 hours. The residue, after distilling off the solvent, is recrystallized from dimethylformamide to yield 2.45 g of 5,6-dihydro-1-oxo-5-thioxo-1H-pyrazolo[1,2-a][1,2,4]benzotriazine-2-carboxylic acid, ethyl ester having a melting point of 277°–282° C.; yellow needles.

EXAMPLE 3

5,6-Dihydro-6-methyl-1,5-dioxo-1H-pyrazolo[1,2-a][1,2,4]benzotriazine-2-carboxylic acid, ethyl ester 5.22 g 5,6-dihydro-1,5-dioxo-1H-pyrazolo[1,2-a][1,2,4]benzotriazine-2-carboxylic acid, ethyl ester, made as in Example 1, 2.76 g $K_2CO_3$ and 50 mM $CH_3I$ are dissolved in 100 ml dimethylformamide and stirred for 20 hours. The crystalline 5,6-dihydro-6-methyl-1,5-dioxo-1H-pyrazolo[1,2-a][1,2,4]benzotriazine-2-carboxylic acid, ethyl ester is isolated after filtration and recrystallized from dimethylformamide/ethanol. The yield is 4.7 g as white needles with a melting point of 243°–244° C.

EXAMPLE 4

6-Ethyl-5,6-dihydro-1,5-dioxo-1H-pyrazolo[1,2-a][1,2,4]benzotriazine-2-carboxylic acid, ethyl ester 5.22 g of 5,6-dihydro-1,5-dioxo-1H-pyrazolo[1,2-a][1,2,4]benzotriazine-2-carboxylic acid, ethyl ester made as in Example 1. 2.76 $K_2CO_3$ and 50 mM $CH_3CH_2I$ are dissolved in 100 ml dimethylformamide and stirred for 20 hours. The crystalline 6-ethyl-5,6-dihydro-1,5-dioxo-1H-pyrazolo[1,2-a][1,2,4]benzotriazine-2-carboxylic acid, ethyl ester is isolated after filtration and recrystallized from dimethylformamide/ethanol. The yield is 4.7 g of white crystals having a melting point of 235°–237° C.

EXAMPLE 5

5,6-Dihydro-1,5-dioxo-1H-pyrazolo[1,2-a][1,2,4]benzotriazine-2-carboxylic acid

To a solution of 3 g of 5,6-dihydro-1,5-dioxo-1H-pyrazolo[1,2-a][1,2,4]benzotriazine-2-carboxylic acid, ethyl ester of hot ethanol, there is added 10 ml of 10% aqueous sodium hydroxide and the mixture refluxed for 2 hours. The mixture is concentrated under reduced pressure and the residue dissolved in water. The solution is filtered and neutralized with dilute hydrochloric acid. The precipitated 5,6-dihydro-1,5-dioxo-1H-pyrazolo[1,2-a][1,2,4]benzotriazine-2-carboxylic acid is filtered and washed with a small amount of cold water. The product is crystallized from ethanol.

EXAMPLE 6

5,6-Dihydro-1,5-dioxo-1H-pyrazolo[1,2-a][1,2,4]benzotriazine-2-carboxylic acid, sodium salt 2.6 g of 5,6-dihydro-1,5-dioxo-1H-pyrazolo[1,2-a][1,2,4]benzotriazine-2-carboxylic acid is dissolved in 100 ml of 0.1 N aqueous sodium hydroxide, the solution is filtered and lyophilized to give 5,6-dihydro-1,5-dioxo-1H-pyrazolo[1,2-a][1,2,4]benzotriazine-2-carboxylic acid, sodium salt.

The following additional products shown in Column I are obtained by the procedure of Examples 1 and 2 by substituting a compound shown in Column II for 1-(2-aminophenyl)-5-hydroxy-1H-pyrazole-4-carboxylic acid, ethyl ester and a compound shown in Column III for 1,1'-carbonyl-bis-[1H-imidazole] (in Example 1) or 1,1'-thiocarbonyl-bis-[1H-imidazole] (in Example 2).

Column I

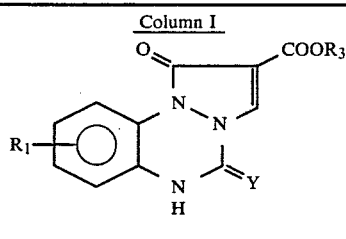

Column II

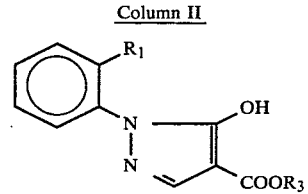

Column III

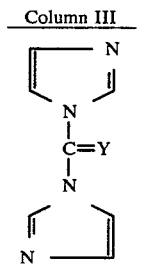

| Example | R₁ | R₃ | Y |
|---|---|---|---|
| 7 | —Cl | —C₂H₅ | O |
| 8 | —Br | —C₂H₅ | O |
| 9 | —CH₃ | —C₂H₅ | O |
| 10 | —NO₂ | —C₂H₅ | O |
| 11 | —OH | —C₂H₅ | O |
| 12 | —H | —C₂H₅ | S |
| 13 | —NH₂ | C₂H₅ | S |
| 14 | —CH₃ | —C₃H₇ | S |
| 15 | —OH | —C₃H₇ | S |

The following additional products shown in Col. IV are obtained by following the procedure of Examples 3 and 4 but substituting a compound shown in Column V for CH₃I (in Example 3) for C₂H₅I (in Example 4) and a compound shown in Column VI for 5,6-dihydro-1,5-dioxo-1H-pyrazolo[1,2-a][1,2,4]benzotriazine-2-carboxylic acid, ethyl ester.

Column IV

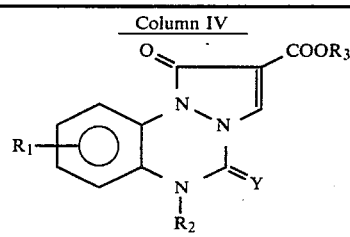

Column V

R₂—I

Column VI

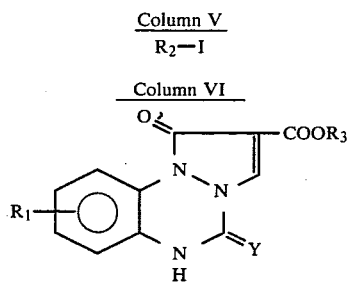

| Example | R₁ | R₂ | R₃ | Y |
|---|---|---|---|---|
| 16 | —CH₃ | —CH₃ | —C₂H₅ | O |
| 17 | —Cl | —C₂H₅ | —C₂H₅ | O |
| 18 | —H | —C₃H₇ | —C₂H₅ | O |
| 19 | —OH | | —C₂H₅ | O |
| 20 | —NH₂ | —CH₂—C₆H₅ | —C₂H₅ | S |
| 20 | —NH₂ | —C₄H₉ | —C₂H₅ | S |

The following additional products shown in Column VII are obtained by following the procedure of Example 5 but substituting the product of Example 1, 3 or 4 or a compound shown in Column I or IV of Examples 7-20 for 5,6-dihydro-1,5-dioxo-1H-pyrazolo[1,2-a][1,2,4]benzotriazine-2-carboxylic acid, ethyl ester in Example 5.

Column VII

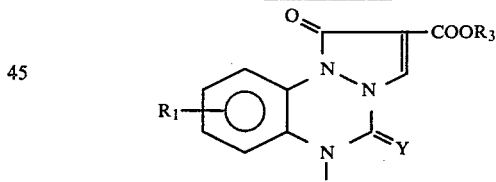

| Example | R₁ | R₂ | R₃ | Y |
|---|---|---|---|---|
| 21 | —CH₃ | —H | —H | O |
| 22 | —H | —H | —H | O |
| 23 | —H | —CH₃ | —H | O |
| 24 | —H | —C₂H₅ | —H | O |
| 25 | —Cl | —H | —H | O |
| 26 | —OH | —H | —H | O |
| 27 | —NH₂ | —H | —H | O |
| 28 | —NH₂ | —H | —H | S |
| 29 | —OH | —H | —H | S |
| 30 | —CH₃ | —H | —H | S |
| 31 | —H | —H | —H | S |

The following additional products shown in Column VIII are obtained by following the procedure of Example 6 but substituting a compound shown in Column VII of Example 21-31 for 5,6-dihydro-1,5 dioxo-1H-pyrazolo[1,2-a][1,2,4]benzotriazine-2-carboxylic acid in Example 6, and a compound shown in Column IX for NAOH in Example 6 where n is 1 or 2.

Column VIII

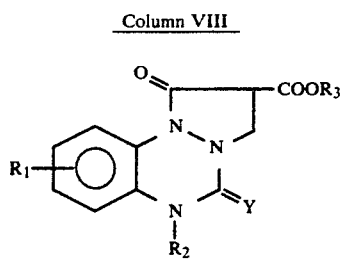

Column IX $R_3(OH)_n$

| Example | $R_1$ | $R_2$ | $R_3$ | Y |
|---------|-------|-------|-------|---|
| 32 | —H | —$C_2H_5$ | Na | O |
| 33 | —Cl | —H | Na | O |
| 34 | —OH | —H | Na | O |
| 35 | —$CH_3$ | —H | Na | O |
| 36 | —H | —H | K | O |
| 37 | —$NH_2$ | —H | K | O |
| 38 | —Cl | —H | K | O |
| 39 | —OH | —H | K | O |
| 40 | —H | —H | Ca | S |
| 41 | $NH_2$ | —H | Ca | S |
| 42 | —H | —H | Mg | S |
| 43 | $NH_2$ | —H | Mg | S |

What is claimed is:

1. A compound of the formula

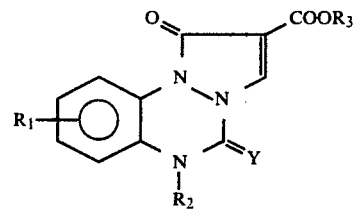

wherein
$R_1$ is hydrogen, lower alkyl, nitro, amino, lower alkyl-amino, di(lower alkyl) amino, $SR_4$, $OR_4$ or halogen;
$R_2$ is hydrogen, lower alkyl or aralkyl;
$R_3$ is hydrogen, lower alkyl or a salt forming ion; $R_4$ is hydrogen or lower alkyl; and Y is oxygen or sulfur.

2. A compound as in claim 1 wherein $R_1$ is hydrogen; $R_2$ is hydrogen or lower alkyl; $R_3$ is hydrogen, lower alkyl or salt forming ion and said salt forming ion is an alkali metal or alkaline earth; $R_4$ is hydrogen; and Y is oxygen.

3. The compound of claim 2 wherein
$R_1$ is hydrogen;
$R_2$ is hydrogen or lower alkyl;
$R_3$ is hydrogen, lower alkyl or alkali metal;
$R_4$ is hydrogen; and Y is oxygen.

4. The compound of claim 1 wherein $R_1$ is hydrogen, lower alkyl, nitro, Cl, Br, —OH, amino, lower alkyl-amino, or di(lower alkyl)amino.

5. A compound as in claim 1, wherein $R_1$ is hydrogen.

6. A compound as in claim 5 wherein $R_3$ is ethyl.

7. A compound as in claim 6, 5,6-dihydro-1-oxo-5-thioxo-1H-pyrazolo[1,2-a][1,2,4]benzotriazine-2-carboxylic acid, ethyl ester.

8. A compound as in claim 6, 5,6-dihydro-1,5-dioxo-1H-pyrazolo[1,2-a][1,2,4]benzotriazine-2-carboxylic acid, ethyl ester.

9. A compound as in claim 6, 5,6-dihydro-6-methyl-1,5-dioxo-1H-pyrazolo[1,2-a][1,2,4]benzotriazine-2-carboxylic acid, ethyl ester.

10. A compound as in claim 6, 6-ethyl-5,6-dihydro-1,5-dioxo-1H-pyrazolo[1,2-a][1,2,4]benzotriazine-2-carboxylic acid, ethyl ester.

* * * * *

UNITED STATES PATENT AND TRADEMARK OFFICE
CERTIFICATE OF CORRECTION

PATENT NO. : 4,260,751
DATED : April 7, 1981
INVENTOR(S) : Uwe D. Treuner

It is certified that error appears in the above-identified patent and that said Letters Patent are hereby corrected as shown below:

In Column 4, line 7, "$R_2$" should be -- $R_3$ --.

In Column 7, line 40,

"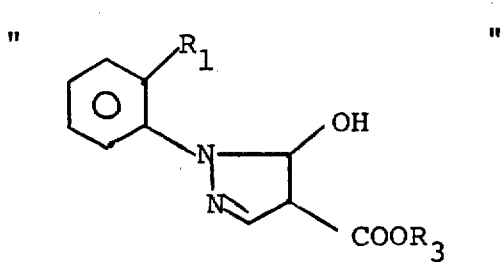"

should read:

-- 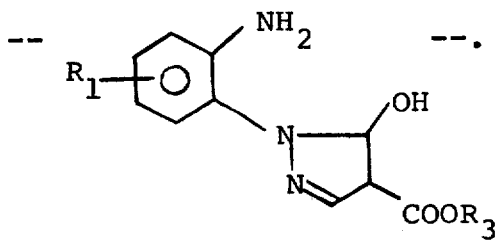 --.

Signed and Sealed this

Eighth Day of September 1981

[SEAL]

Attest:

Attesting Officer

GERALD J. MOSSINGHOFF
Commissioner of Patents and Trademarks